United States Patent
Muller et al.

(10) Patent No.: US 6,796,797 B2
(45) Date of Patent: Sep. 28, 2004

(54) DEVICE FOR EXTRACTING A DENTAL APPLIANCE

(76) Inventors: Alexandre Muller, La Tour d'Aygosi, Bat. 8 67 Cours Gambetta, F-13100 Aix-en-Provence (FR); William Muller, 39 Avenue Paul Cezanne, F-13090 Aix-en-Provence (FR)

( * ) Notice: Subject to any disclaimer, the term of this patent is extended or adjusted under 35 U.S.C. 154(b) by 0 days.

(21) Appl. No.: 10/182,580
(22) PCT Filed: Feb. 2, 2001
(86) PCT No.: PCT/FR01/00315
§ 371 (c)(1), (2), (4) Date: Oct. 7, 2002
(87) PCT Pub. No.: WO01/56495
PCT Pub. Date: Aug. 9, 2001

(65) Prior Publication Data
US 2003/0091958 A1 May 15, 2003

(30) Foreign Application Priority Data
Feb. 3, 2000 (FR) .............................. 00 01381
Mar. 27, 2000 (FR) .............................. 00 03833

(51) Int. Cl.⁷ ................................. A61C 3/16
(52) U.S. Cl. ....................................... 433/141
(58) Field of Search ............... 433/141, 150, 433/152, 153, 154, 158, 157, 159, 161, 162; 452/17; 30/120.1

(56) References Cited

U.S. PATENT DOCUMENTS

| | | | | |
|---|---|---|---|---|
| 2,624,942 A | * | 1/1953 | Wilborn | 433/150 |
| 4,179,816 A | * | 12/1979 | Anderson | 433/161 |
| 4,205,664 A | * | 6/1980 | Baccialon | 601/141 |
| 4,594,069 A |   | 6/1986 | Thompson | |

FOREIGN PATENT DOCUMENTS

| | | |
|---|---|---|
| DE | 36 21 055 | 1/1988 |
| DE | 37 33 634 | 4/1989 |
| EP | 0 399 237 | 11/1990 |
| WO | WO 99 39651 | 8/1999 |
| WO | WO 99 44530 | 9/1999 |

* cited by examiner

Primary Examiner—Melba Bumgarner
(74) Attorney, Agent, or Firm—Harrison & Egbert

(57) ABSTRACT

An instrument for removing a crown by generating a couple of forces between the occlusal surface of the stump of the tooth and the basal surface of the crown. The instrument has an indented intermediate portion and a working part extending from a tapered intermediate portion and a handle. When inserted in a groove formed at the occlusal part of the stump along a plane substantially parallel to the occlusal surface of the crown, the working portion enables, by a physical action, exertion of a couple of forces between the respective occlusal surfaces of the stump and the basal surface of the crown. The working part is rotatable integrally and correspondingly with a rotation of the handle.

2 Claims, 6 Drawing Sheets

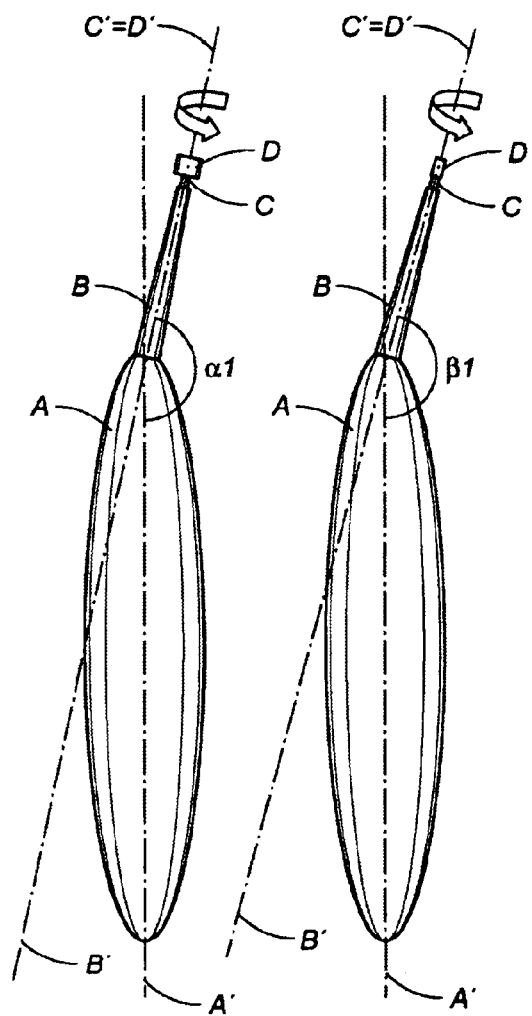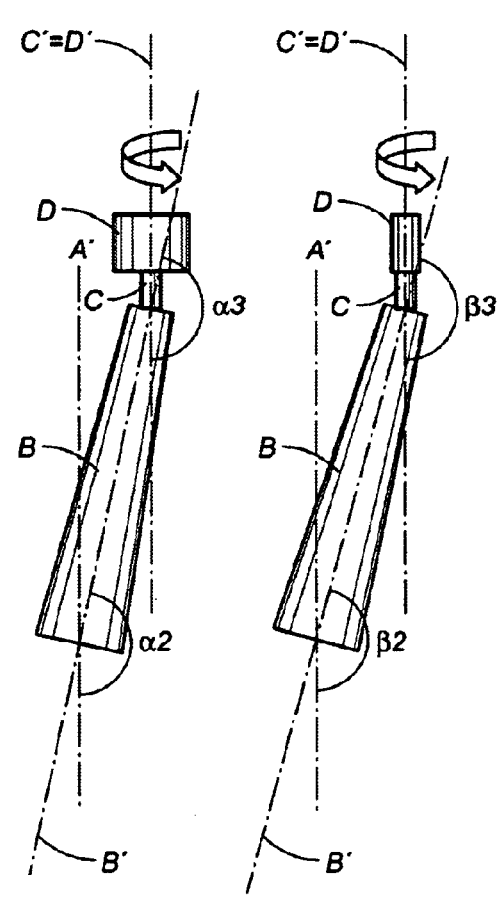
FIG. 12   FIG. 13   FIG. 14   FIG. 15

DEVICE FOR EXTRACTING A DENTAL APPLIANCE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to an alternative or additional solution to dental surgeons and stomatologists to remove individual crowns, bridge supports and other prostheses sealed on natural teeth or implants.

BACKGROUND OF THE INVENTION

The purpose of this invention is to give an alternative or additional solution to dental surgeons and stomatologists to remove individual crowns, bridge supports and other prostheses sealed on natural teeth or implants. Most existing solutions are either of complex implementation, or costly because they cause, on one hand, destruction of the crown (4), and on the other hand, significant wear of the burs and fatigue of the rotary instruments. Furthermore, this is an unpleasant even painful operation for the patient.

It is first to be noted that:

although, in practice, a tooth or an implant is never vertical in the strict sense of the term, for reasons of clarity in the explanations, the verticality reference will be the vertical axis of the tooth (F) or of the implant, as shown in FIGS. 16, 17 and 18;

FIG. 16 shows a cross-section of the tooth along the sagittal plane while FIGS. 17 and 18 show a cross-section of the tooth along the frontal plane; and all figures, embodiments and applications are described based on a prosthesis sealed onto a natural or reconstructed stump (3). However, this invention can perform the same function whenever the stump (3) is prosthetic, especially in the field of implantology. As a convention, the prosthetic system that fits on the implant and on which the crown is set (4) shall be designated as the prosthetic stump (3).

In the field of dental crown removal, one of the means used has been the instrument patented in 1982 under the name of dental instrument designed for the removal of crowns and pivot teeth (Publication No. 2 522 494, National Publication No. 82 03435, date of filing: Mar. 2, 1982). It consisted primarily of a grip and a shank with its front part bent back. That tool and the method used offered the advantage of causing a lever effect between the stump (3) and the crown (4) while sparing the gum and thus enabling to recover the crown (4) whenever the operation was successful. However, the shapes and dimensions of the instrument, and the method used, made it so that the couple of forces generated to achieve the lifting of the crown (4), took place on one hand on the occlusal surface of the stump (3), and on the other hand at the top of the notch (1) made in the face of the crown (4). However, if the seating of the occlusal surface of the stump (3) was located in the vertical axis (F) of the tooth, the force applied on the wall of the crown (4) was then a movement offset in relation to the vertical axis (F) of the tooth. This resulted in a lateral force that was harmful to the dent or implant.

Another device published under reference EP 0 399 237 has this same disadvantage of generating a tilting movement of the prosthesis in relation to the stump because of the actuation of flat and protruding shapes.

On the contrary, this invention makes it possible to achieve an even couple of forces, limiting or eliminating any lateral force because the latter is in an axis that coincides fully or almost fully with the vertical axis (F) of the tooth or implant.

BRIEF SUMMARY OF THE INVENTION

This invention consists of an instrument containing an indented intermediate part (C) and a working part (D). Inserted into a groove (2) made beforehand by the practitioner, the working part (D) is designed to generate a couple of forces roughly in the vertical axis (F) of the tooth or implant between the occlusal faces of the stump (3) on one hand, and the basal surface of the crown (4) on the other hand, thus causing the removal of the crown (4). Until the crown (4) is unsealed, the shapes and dimensions of the indented intermediate part (C) enable it not to hinder the lifting of the notched sidewall of the crown (4) and not to apply any lateral forces on the crown (4).

BRIEF DESCRIPTION OF THE SEVERAL VIEWS OF THE DRAWINGS

FIGS. 12 and 13 are schematic views of another embodiment of the present invention with a face angle and profile angle.

FIGS. 14 and 15 are schematic views of another embodiment of the present invention with different face angles and profile angles.

DETAILED DESCRIPTION OF THE INVENTION

This invention consists of an instrument containing an indented intermediate part (C) and a working part (D). Inserted into a groove (2) made beforehand by the practitioner, the working part (D) is designed to generate a couple of forces roughly in the vertical axis (F) of the tooth or implant between the occlusal faces of the stump (3) on one hand, and the basal surface of the crown (4) on the other hand, thus causing the removal of the crown (4). Until the crown (4) is unsealed, the shapes and dimensions of the indented intermediate part (C) enable it not to hinder the lifting of the notched sidewall of the crown (4) and not to apply any lateral forces on the crown (4).

Figure 16:
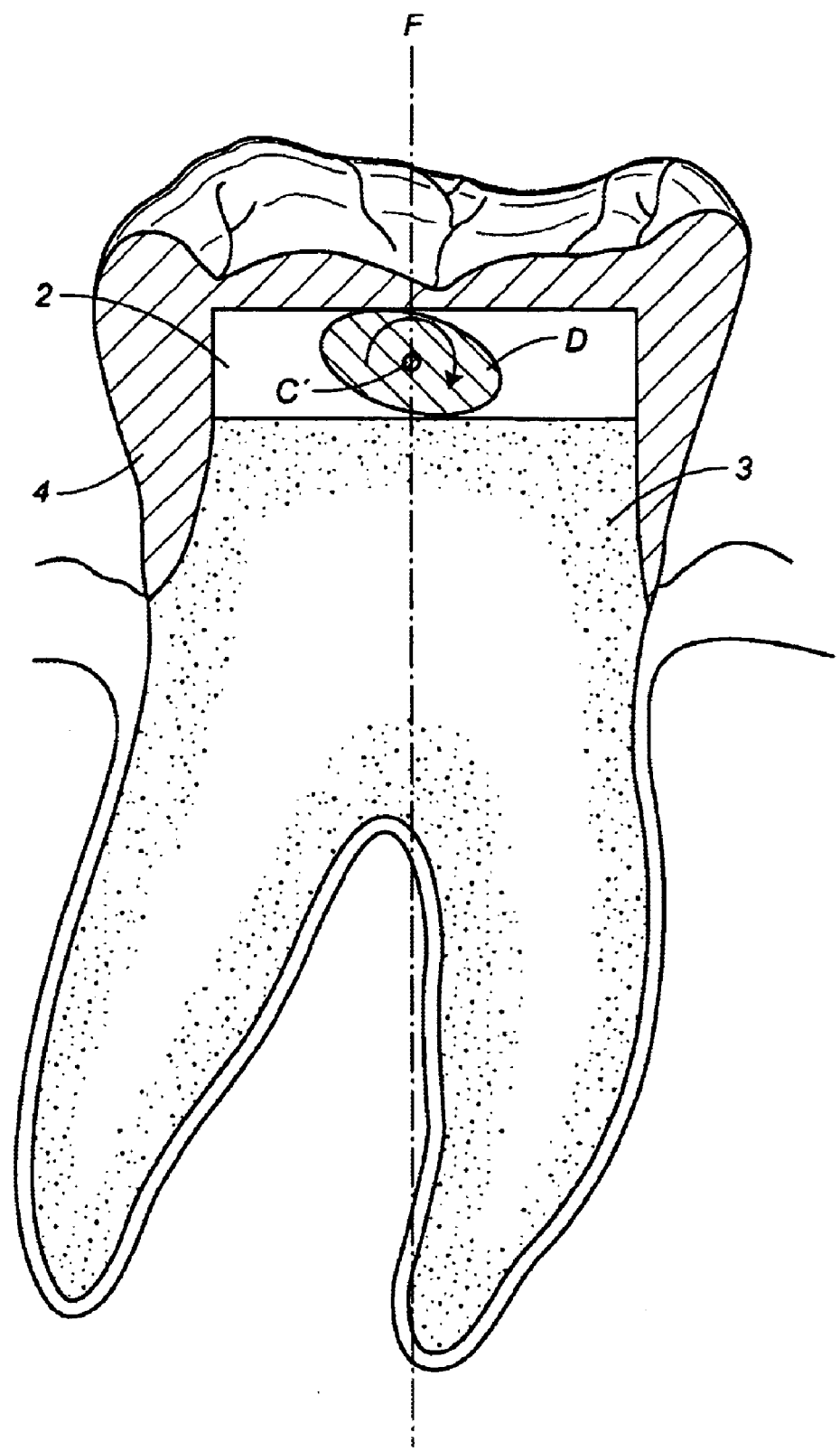
FIG. 16 shows a cross-sectional view of the present invention in a tooth in the sagittal plane.
Figure 17:
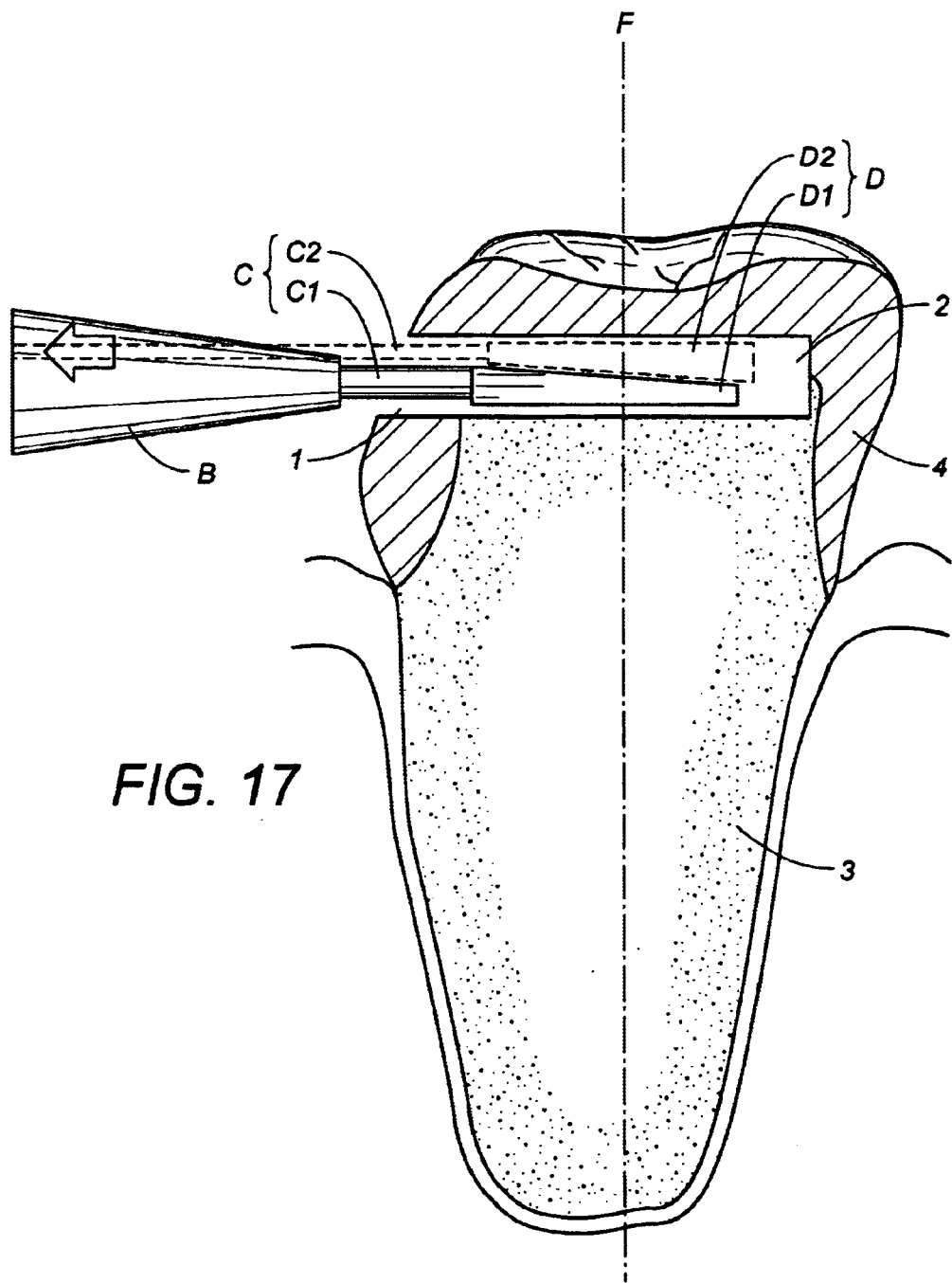
FIGS. 17 and 18 are cross-sectional views of the present invention in a tooth along the frontal plane of the tooth.
Figure 18:
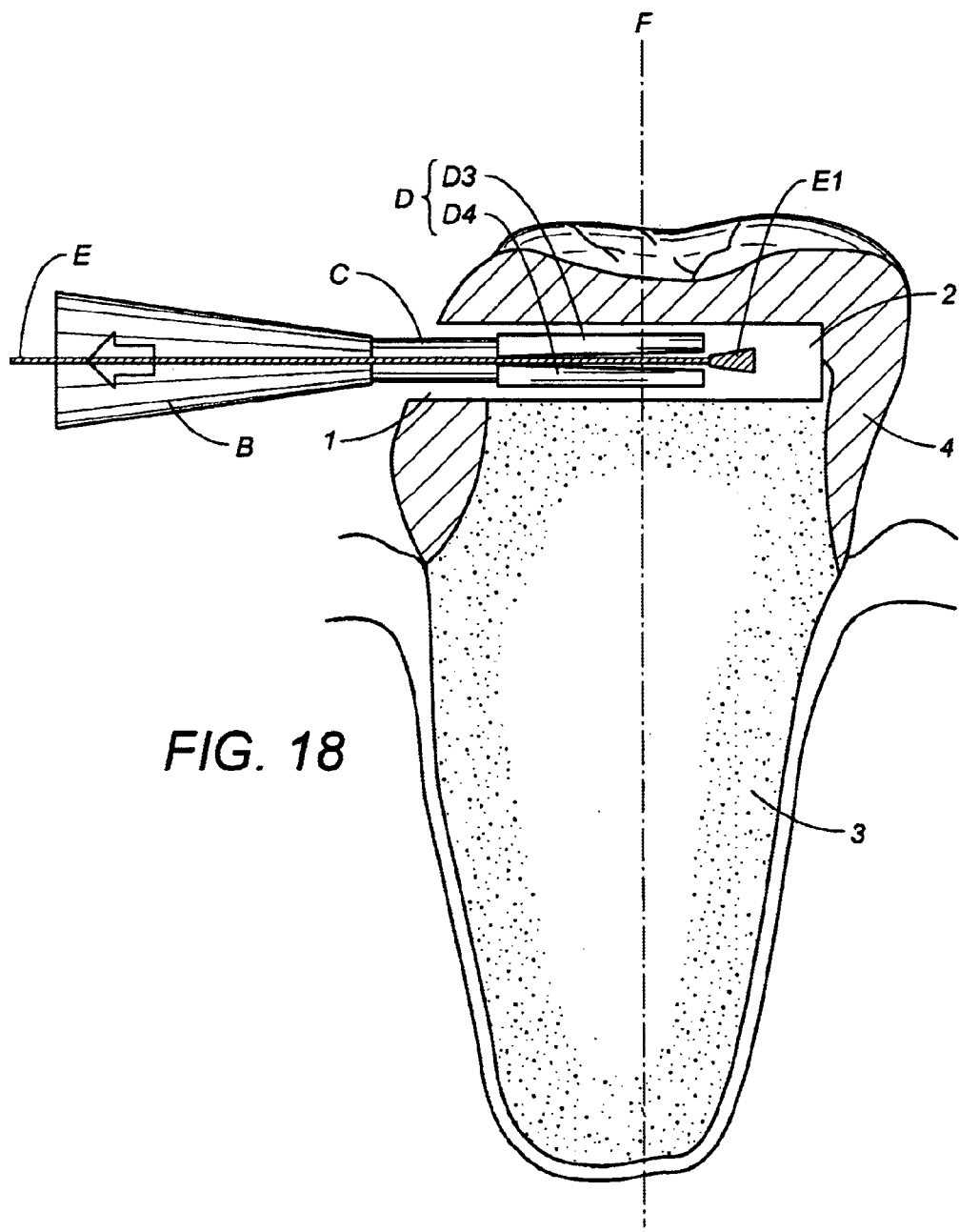

The invention requires in its application four operations common to all alternative designs [see FIGS. 16, 17 and 18].

The use of the instrument requires making beforehand a notch (1) through the thickness of the crown (4) on its most accessible face (generally, the vestibular face). This notch (1) must have a width greater than or equal to the diameter of the indented intermediate part (C). This notch (1) must be made on a plane roughly parallel to the occlusal surface of the crown (4) at the assumed level of the occlusal part of the stump (3).

In a second step, said notch (1) is extended using a bur (of the fissure type) to create a groove (2) through partial or full sweeping of the stump (3). Said groove (2) must have dimensions allowing for full introduction of the working part (D).

In a third step, the working part (D) of the instrument should be slid into the groove (2) thus created until the indented intermediate part (C) coincides with the notch (1) in the crown (4).

Finally, the crown (4) lifting mechanism is actuated, which may result from an expansion or rotation of the working part (D) or from any other process causing a couple of forces roughly in the axis of the tooth (or of the implant) between the occlusal faces of the stump (3) on one hand and of the basal surface of the crown (4) on the other hand.

Thus, proper use of the instrument makes it possible to unseal the crown (4) with minimum lateral forces that are inefficient, painful and detrimental to the preservation of the stump (3), tooth or implant.

In addition, in the process used, the crown (4) is cut in a plane roughly parallel to the occlusal surface of the crown (4), which makes it possible not to destroy the crown (4). As a matter of fact, the notch (1) made into the crown (4) preserves its rigidity and does not alter its cervical setting, which permits to recover it so that it can possibly be put back in place. After putting the crown (4) back in place, all is needed is to plug the notch (1) using proper materials.

The list of methods that can be used to apply a couple of forces between the occlusal faces of the stump (3) and the basal surface of the crown (4) is not exhaustive. A limited number of embodiments compared to the number of practicable technical processes will be described.

As non-limiting examples, in addition to the embodiments described below, the invention can take the form of an instrument whose working part (D) will be made of a material that offers controlled expansion capabilities, whose roughly vertical expansion will be achieved, in a non-limiting example, through temperature variation.

As a matter of fact, all physical processes inducing a roughly vertical expansion of the working part (D) can be considered, provided the instrument is characterized by the presence of an indented intermediate part (C) allowing for free lifting of the crown (4) and the absence or limitation of lateral forces. The shank (A) and the intermediate section (B) will be accessorily required only to hold or to actuate the working part (D) inside groove (2), depending on the expansion system used (for example, the shank (A) and the tapered intermediate section (B) are necessary to hold and rotate the working part (D) of the R.U.I. described later).

For an easier use, the invention can be equipped with a mechanism allowing for an easy, even automatic, return to the rest position of the working part (D). A mechanism such as a motor or turbine, can also initiate successively the vertical expansion of the working part (D) and then its return to the rest position.

The instrument may require some adjustment to the various situations encountered (dimension and more or less accessible position of the tooth to be treated). Such adjustment can be achieved through modulation in the alignment of its different parts or in the shapes and dimensions of said parts. Thus, the instrument may advantageously take the form of a set of interchangeable end pieces incorporating one or more parts of the instrument.

The focus will be on describing more specifically three embodiments of the invention: a rotary unsealing instrument (R.U.I); an alternative design using the overlapping of two inclined planes (O.T.I.P.) [see FIG. 17]; and an alternative design with vertical expansion (V.E.) [see FIG. 18].

The R.U.I. can be broken down into 4 parts (FIGS. 1 and 2): a shank (A); a tapered intermediate section (B); an indented intermediate part (C); and a working part (D).

The R.U.I. shank (A) has an ergonomic shape designed to be held in the hand and to actuate the instrument rotation, in a manner similar to the shank of a syndesmotome.

The only function of the R.U.I tapered intermediate section (B) is to make the transition from the section of the shank (A) to a section close or equal to that of the indented intermediate part (C). Its shapes and dimensions can thus be varied.

The R.U.I. indented intermediate part (C) comes in the form of a segment with a preferably cylindrical shape. Its diameter depends on the dimensions of the notch (1) made in crown (4). Its length depends on the thickness of the crown (4) and on the depth of the groove (2).

The R.U.I. working part can take the most varied shapes provided, through rotation of the R.U.I, they generate a couple of forces between the occlusal faces of the stump (3), on one hand, and of the basal surface of the crown (4), on the other hand. This implies that the distance between the lateral ends of the working part (D) is greater than the height of the groove (2).

Whether in its cross-section, face or profile, the R.U.I. working part (D) can be given specific shapes, including rectangular, ovoid, triangular, snail-shaped or lozenge-shaped. However, the cross-section of the working part will preferably be ovoid or snail-shaped. Such shapes will indeed provide for an even, non-traumatizing, lifting closer to the axis (F) of the tooth because of the absence of protruding parts and the proximity between the points where the couple of forces is applied and the center of the tooth.

In addition, as the working part (D) can have different shapes and sizes, the R.U.I. can advantageously come in the form of a set of interchangeable end pieces. Depending on the location chosen to operate the anchoring system, each end piece can incorporate one or more parts of the instrument.

Figure 1:
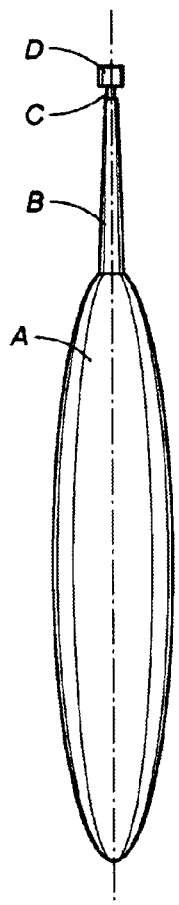
FIG. 1 is a front schematic view of the present invention.
Figure 2:
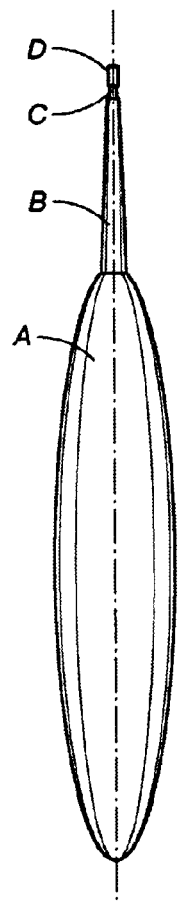
FIG. 2 is a side schematic view of the present invention as shown in FIG. 1.

The angles between axes A', B', C' and D' of the R.U.I. various parts can be different so that all parts of the R.U.I. can be either on one same axis [see FIGS. 1 and 2], or different axes for easier handling inside the mouth, as for example for posterior teeth [see FIGS. 12, 13, 14 and 15].

Figure 3:
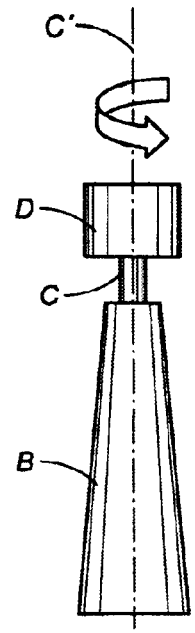
FIG. 3 is a front schematic view of another embodiment of the present invention.
Figure 4:
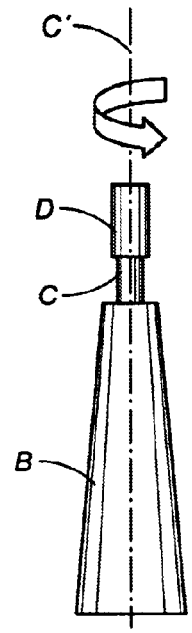
FIG. 4 is a side schematic view of the present invention as shown in FIG. 3.

FIGS. 3 and 4 show an alternative design of R.U.I. end piece with a working part (D) whose face (FIG. 3) and profile (FIG. 4) are rectangular respectively, with the ends diametrically and symmetrically opposite in relation to the axis of rotation (CÆ) of the indented intermediate part (C).

Figure 5:
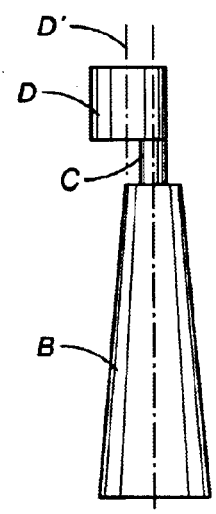
FIG. 5 is a front schematic view of still another embodiment of the present invention.

FIG. 5 shows an alternative design of R.U.I. with a working part (D) in the shape of a "blank key". The axis of rotation (D') of the working part (D) is parallel to the axis (C') of the indented intermediate part (C), but separate from it.

Figure 6:
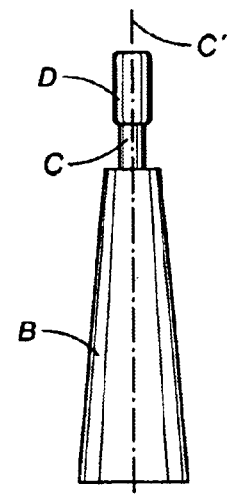
FIG. 6 is another side schematic view of the present invention with rounded edges.

FIG. 6 shows an alternative design of R.U.I. with a working part (D) whose profile has a rectangular shape with rounded edges.

Figure 7:
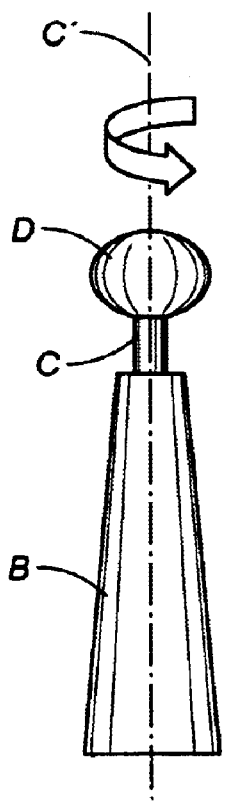
FIGS. 7, 8 and 9 are schematic views of the present invention with an ellipsoidal shape.
Figure 8:
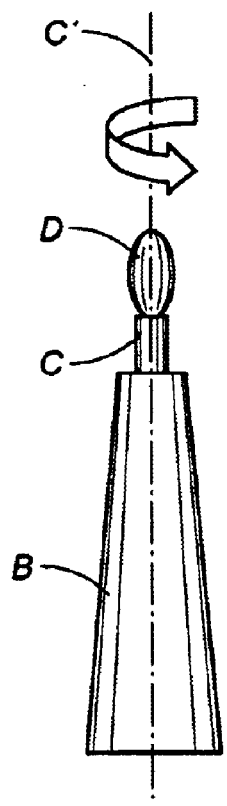
Figure 9:

FIGS. 7, 8 and 9 show an alternative design of R.U.I. end piece with a working part (D) whose face (FIG. 7), profile (FIG. 7) and cross-section (FIG. 9) are ellipsoidal.

Figure 10:
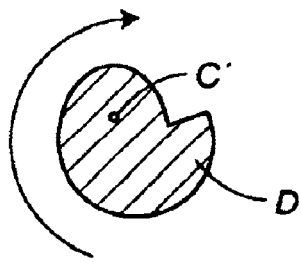
FIGS. 10 and 11 are isolated cross-sectional views of the present invention.

FIG. 10 shows an alternative design of the R.U.I. working part (D) whose cross section is snail-shaped. This shape offers the advantage of achieving an even couple of forces, toughly vertical and very close to the vertical axis (F) of the tooth.

Figure 11:

FIG. 11 shows the cross-section of a R.U.I. indented intermediate part (C) of cylindrical shape.

FIGS. 12 and 13 show an alternative design of R.U.I. whose axes A' of the handle (A) and B' of the tapered intermediate section (B) form face angle $\alpha 1$ and profile angle $\beta 1$.

FIGS. 14 and 15 show an alternative design of R.U.I. whose axes A' of the handle (A) and B' of the tapered intermediate section (B) form face angle $\alpha 2$ and profile angle $\beta 2$ and whose axes B' and C' of the indented intermediate section (C) form face angle $\alpha 3$ and profile angle $\beta 3$.

FIG. 16 shows an alternative design of R.U.I. whose working part (D) has a rectangular section that, once inserted into groove (2), permits to generate through rotation a couple of forces between the basal surface of the occlusal face of the crown (4) and the occlusal face of the stump (3). FIG. 16 shows a cross-section of the tooth along the sagittal plane.

After having made the notch (1) and the groove (2), the R.U.I. working part (D) is inserted into the groove (2) so that the indented intermediate part (C) is positioned at the notch (1) made in the prosthesis. The shapes and dimensions of the indented intermediate part (C) enable it to freely make rotation movements that it transmits to the working part (D).

The assembly thus achieved permits to transmit to the working part (D) the rotation movements successively applied by the practitioner at the handle (A).

The respective dimensions of the indented intermediate part (C) and of the working part (D) can vary based on the situations encountered, whether dealing with a standard crown or a crown on implant. As a non-limiting example, the indented intermediate part (C), as represented in FIG. 3, can come in the form of an approx. 4 mm to 5 mm long cylinder with a section from 1 mm to 1.6 mm and the working part (D) can take the form of a rectangular parallelepiped whose thickness is roughly equal to the diameter of the indented intermediate part (C) (i.e., 1 to 1.6 mm) whose non-sharp edges are 1.6 to 3 mm.

The alternative design using the overlapping of two inclined planes (O.T.I.P) consists of: a handle (A); a tapered intermediate part (B); an indented intermediate part (C); and a working part (D) split into (D1) and (D2).

The handle (A) of the O.T.I.P. has characteristics roughly identical to those of the R.U.I. However, it includes in addition the insertion of a mechanism designed to actuate the working half-part (D2). This mechanism can also contain a system allowing for the O.T.I.P.'s automatic return to the rest position.

The characteristics of the tapered intermediate section (B) on the O.T.I.P. are roughly identical to those of the R.U.I. However, it includes in addition the insertion of the device designed to initiate the movement of the working half-part (D2).

The indented intermediate part (C) of the O.T.I.P. consists of two parts sliding on each other or into each other. The first part (C1) is integral on one hand with the tapered intermediate section (B), on the other hand with the lower pentahedron (D1) of the working part (D). The second part (C2) is integral on one hand with the mechanism inserted in the handle (A) that imparts movement and runs through the tapered intermediate section (B), on the other hand with the upper pentahedron (D2) of the working part (D). The shapes and dimensions of the indented intermediate part (C) must allow for a vertical translation of the crown (4).

The working part (D) of the O.T.I.P. consists of two half-parts (D1) and (D2), featuring each an inclined plane whose sum, when the O.T.I.P. is in rest position, forms a rectangular parallelepiped. Each of the two half-parts (D1) and (D2) overall has the shape of a pentahedron.

As in the case of the R.U.I., after having made the notch (1) and the groove (2), the working part (D) of the O.T.I.P. at rest is inserted into the groove (2) so that the indented intermediate part (C) is positioned at the notch (1) made in the prosthesis.

Whenever, using the device inserted into handle (A), a pull action is applied to the pentahedron D2, the latter, when overlapping pentahedron D1, rises evenly so that pentahedrons D1 and D2 generate a roughly vertical expansion of the working part (D). With the pentahedron D1 pressed against the occlusal face of the stump (3) and with the pentahedron D2 pressed against the occlusal face of the basal surface of the crown (4), a couple of forces is achieved between both faces.

The alternative design with vertical expansion (V.E.) [see FIG. 18] includes: a handle (A); a shank (E); a tapered intermediate part (B); an indented intermediate part (C); and a working part (D) split into (D3) and (D4).

The handle (A) of the V.E. has characteristics roughly identical to those of the R.U.I. However, it includes in addition the insertion of a mechanism allowing for the actuation of a shank (E) extending into the working part (D). This mechanism can also include a system allowing for automatic return of the V.E. to the rest position.

The shank (E) is inserted into the V.E. It has a wide end (E1) so that whenever a pull action is applied onto the shank (E) from the handle (A), the wide end (E1) becomes lodged between the polyhedrons (D3) and (D4) causing them to be pulled apart.

The characteristics of the tapered intermediate section (B) of the V.E. are roughly identical to those of the R.U.I. However, it also includes in addition insertion of the shank (E).

The indented intermediate section of the V.E. has characteristics roughly identical to those of the R.U.I. However, it also includes in addition insertion of the shank (E).

The working part (D) of the V.E. consists of two polyhedrons (D3) and (D4) with two inclined planes opposite to the wide end (E1) of the shank (E). Whenever the shank (E) is pulled between the inclined planes, their gradual separation is achieved, and thus the roughly vertical expansion of the working part (D).

A notch (1) and a groove (2) are made in the same manner as for the R.U.I. The whole V.E. working part (D) is inserted into the groove (2) so that the indented intermediate part (C) is positioned at the notch (1). By actuating the mechanism located in the handle A, a pull action is applied on the wide end (E1) of the shank (E). The wide end (E1) causes a gradual separation of the tow polyhedrons (D3) and (D4) until a couple of forces is achieved between the occlusal face of the basal surface of the crown (4), on one hand, and the occlusal face of the stump (3), on the other hand.

We claim:

1. An instrument for removing a dental crown by being placed in a groove formed at an occlusal face of a natural or prosthetic stump of a tooth along a plane parallel to an occlusal surface of the dental crown, the instrument comprising:

a handle;

a tapered intermediate section extending outwardly from an end of said handle;

an indented intermediate part extending from an end of said tapered intermediate section opposite said handle; and a working means formed at an end of said indented intermediate part opposite said tapered intermediate section, said working means having a size suitable for fitting in the groove, said working means for applying a couple of forces along a vertical axis of the crown between the occlusal face of the stump and a basal surface of the crown by a physical action imparted onto said handle, said indented intermediate part having a shape and dimensions associated therewith defined so as to limit lateral forces on the crown while not hindering a vertical translation of a notched wall of the crown, said indented intermediate part rotatable integrally and correspondingly with said tapered intermediate section and said handle upon an application of a rotation to said handle, said working means being a part having an ellipsoidal cross-section or an oval cross-section or a snail-shaped cross-section.

2. The instrument of claim 1, at least two of said working means and said indented intermediate part and said tapered intermediate section and said handle being located on axes forming obtuse angles between one anther.

* * * * *